(12) United States Patent
Shimizu et al.

(10) Patent No.: US 12,728,247 B2
(45) **Date of Patent: *Sep. 8, 2026**

(54) MICRONEEDLE DEVICE AND METHOD FOR PRODUCING SAME

(71) Applicant: HISAMITSU PHARMACEUTICAL CO., INC., Tosu (JP)

(72) Inventors: Tatsuya Shimizu, Tsukuba (JP); Takako Esu, Tsukuba (JP); Shinpei Nishimura, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 914 days.

This patent is subject to a terminal disclaimer.

(21) Appl. No.: 17/788,019

(22) PCT Filed: Dec. 18, 2020

(86) PCT No.: PCT/JP2020/047533

§ 371 (c)(1),
(2) Date: Jun. 22, 2022

(87) PCT Pub. No.: WO2021/132100

PCT Pub. Date: Jul. 1, 2021

(65) Prior Publication Data

US 2023/0045891 A1 Feb. 16, 2023

(30) Foreign Application Priority Data

Dec. 23, 2019 (JP) ................................ 2019-231917

(51) Int. Cl.
*A61K 31/137* (2006.01)
*A61K 9/00* (2006.01)
(Continued)

(52) U.S. Cl.
CPC ....... *A61M 37/0015* (2013.01); *A61K 9/0021* (2013.01); *A61K 31/137* (2013.01);
(Continued)

(58) Field of Classification Search
CPC ...... A61M 37/0015; A61M 2037/0023; A61M 2037/0046; A61M 2037/0053;
(Continued)

(56) References Cited

U.S. PATENT DOCUMENTS 5,124,157 A 6/1992 Colley et al.
8,242,158 B1 8/2012 Roychowdhury et al.
(Continued)

FOREIGN PATENT DOCUMENTS

CN 1863571 A 11/2006
CN 102112151 A 6/2011
(Continued)

OTHER PUBLICATIONS

Espacenet English Translation of WO2018123982A1 Claims (Year: 2025).*

(Continued)

*Primary Examiner* — Bethany P Barham
*Assistant Examiner* — Alexandra Nicole Isnor
(74) *Attorney, Agent, or Firm* — Nath, Goldberg & Meyer; Joshua B. Goldberg

(57) ABSTRACT

The present invention aims to provide a method for producing a microneedle device comprising a coating comprising dexmedetomidine and isoproterenol, in which the stability of isoproterenol during production and after production of the microneedle device is high. A method for producing a microneedle device according to one embodiment of the present invention comprises coating microneedles with a coating liquid to form a coating on the microneedles. The microneedle device comprises a substrate, microneedles
(Continued)

disposed on the substrate, and a coating formed on the microneedles. The coating liquid comprises dexmedetomidine or a pharmaceutically acceptable salt thereof, isoproterenol or a pharmaceutically acceptable salt thereof, ethylenediaminetetraacetic acid or a pharmaceutically acceptable salt thereof, and a sulfated polysaccharide.

2 Claims, 2 Drawing Sheets

(51) Int. Cl.
*A61K 31/4174* (2006.01)
*A61K 47/18* (2017.01)
*A61K 47/36* (2006.01)
*A61L 31/08* (2006.01)
*A61L 31/16* (2006.01)
*A61M 37/00* (2006.01)

(52) U.S. Cl.
CPC ........ *A61K 31/4174* (2013.01); *A61K 47/183* (2013.01); *A61K 47/36* (2013.01); *A61L 31/08* (2013.01); *A61L 31/16* (2013.01); *A61L 2420/02* (2013.01); *A61M 2037/0023* (2013.01); *A61M 2037/0046* (2013.01); *A61M 2037/0053* (2013.01); *A61M 2205/0238* (2013.01)

(58) Field of Classification Search
CPC ......... A61M 2205/0238; A61K 9/0021; A61K 31/137; A61K 31/4174; A61K 47/183; A61K 47/36; A61K 47/18; A61L 31/08; A61L 31/16; A61L 2420/02; A61L 2300/436; A61L 2300/45; A61L 31/10; A61L 2300/40; A61L 2300/606; A61P 25/20
USPC .......................................................... 424/443
See application file for complete search history.

(56) References Cited

U.S. PATENT DOCUMENTS

2008/0233179 A1 9/2008 Grenier et al.
2011/0288485 A1 11/2011 Tokumoto et al.
2012/0095104 A1 4/2012 Zachar et al.
2013/0041330 A1 2/2013 Matsudo et al.
2014/0066842 A1* 3/2014 Zhang ..................... A61P 43/00 604/512
2015/0098980 A1 4/2015 Pongpeerapat et al.
2016/0001053 A1 1/2016 Quan et al.
2016/0128944 A1* 5/2016 Chawrai ................ A61K 8/368 514/159
2016/0271380 A1 9/2016 Poon et al.
2017/0080196 A1 3/2017 Lee et al.
2017/0266427 A1 9/2017 Nishimura et al.
2019/0350840 A1* 11/2019 Hori ................... A61K 31/4174
2021/0267882 A1 9/2021 Hori et al.

FOREIGN PATENT DOCUMENTS

CN 102300566 A 12/2011
CN 102395354 A 3/2012
CN 102770176 A 11/2012
CN 103402496 A 11/2013
CN 105073180 A 11/2015
CN 103402496 B 1/2016
CN 105764494 A 7/2016
CN 107106658 A 8/2017
CN 110114069 A 8/2019
CN 110201297 A 9/2019
EP 2540337 A1 1/2013
EP 3560495 A1 10/2019
JP 63-79820 A 4/1988
JP 5-503916 A 6/1993
JP 2001-506904 A 5/2001
JP 2010-029634 A 2/2010
JP 2012-90767 A 5/2012
JP 2014-507473 A 3/2014
JP 2014-508746 A 4/2014
JP 2014-79557 A 5/2014
JP 2016-83085 A 5/2016
JP 2016-532642 A 10/2016
JP 2016-196510 A 11/2016
JP 2017-105784 A 6/2017
JP 2017514646 A 6/2017
JP 2017158938 A 9/2017
KR 20120138235 A 12/2012
KR 20140013022 A 2/2014
KR 20150118136 A 10/2015
KR 20150126413 A 11/2015
KR 101745682 B1 6/2017
TW 201309331 A 3/2013
TW I519781 B 2/2016
WO 98/28037 A1 7/1998
WO 2010013601 A1 2/2010
WO 2010/063030 A2 6/2010
WO WO-2012115207 A1 * 8/2012 ............. A61K 31/00
WO 2012122162 A1 9/2012
WO 2013103378 A1 7/2013
WO WO-2016039418 A1 * 3/2016 ........... A61K 47/183
WO 2016155082 A1 10/2016
WO 2017159767 A1 9/2017
WO 2017180788 A1 10/2017
WO WO-2018123982 A1 * 7/2018 ........... A61K 31/135
WO 2020004234 A1 1/2020

OTHER PUBLICATIONS

Espacenet English Translation of WO2018123982A1 Description (Year: 2025).*
Espacenet English Translation of WO2012115207A1 Description (Year: 2025).*
Google English Translation of WO2016039418A1 (Year: 2025).*
Extended European Search Report dated Feb. 24, 2022 corresponding to application No. 19824984.9.
Korean Office Action dated Jan. 26, 2022 corresponding to application No. 10-2020-7028243.
International Preliminary Report on Patentability dated Jan. 7, 2021 corresponding to application No. PCT/JP2019/024586.
Chinese Office Action dated Mar. 2, 2022 corresponding to application No. 201980042132.1.
Taiwanese Office Action dated Jan. 18, 2021 corresponding to Patent Application No. 108122138.
Extended European Search Report dated Jan. 9, 2024 corresponding to application No. 20906105.0-1109.
Non-Final Office Action dated Feb. 16, 2024 corresponding to U.S. Appl. No. 17/253,311.
Office Action dated Nov. 1, 2022 corresponding to Japanese Patent Application No. P2020-527464.
Notice of Allowanced dated May 31, 2023 corresponding to Chinese application No. 201980042132.1.
Feng Nianping, “Chinese Medicine Percutaneous Administration And Functional Cosmetics”, China Pharmaceutical Science and Technology Press, May 31, 2019, p. 123, the 4th line-p. 125.
Office Action dated Jul. 28, 2023 corresponding to CN Patent Application No. 202080089038.4.
Smith, G. et al., “Effects of ascorbic acid and disodium edetate on the stability of isoprenaline hydrochloride injection”, Journal of Clinical and Hospital Pharmacy, 1984, vol. 9, p. 209-p. 215.
Zhu, et al. “Research Progress in Transdermal Deliver Technology of Micro Needle”; 2016.
Office Action dated Aug. 26, 2021 corresponding to Chinese application No. 201780080926.8.
International Preliminary Report on Patentability (IPRP) dated Jul. 2, 2019 issued in corresponding International Application No. PCTJP2017/046456.

(56) References Cited

OTHER PUBLICATIONS

Office Action dated Jan. 2, 2020 corresponding to Taiwanese application No. 106145761.
Kivisto, K . T. et al."Pharmacokinetics and pharmacodynamics of transdermal dexmedetomidine", European Journal of Clinical Pharmacology; Springer Verlag, DE; vol. 46, No. 4; Jan. 1, 1994; p. 345-p. 349, XP008124147.
Extended European Search Report dated Jul. 3, 2020 corresponding to application No. 17888272.6-1109.
Korean Office Action dated Jan. 19, 2021 corresponding to Patent Application No. 10-2019-7018463.
International Search Report dated Feb. 6, 2018 issued in corresponding International Application No. PCT/JP2017/046456.
Sodium Metabisulfite, retrieved from the Internet at https://en.wikipedia.org/wiki/Sodium_metabisulfite on Mar. 24, 2020. (Year: 2020).
English Translation of JP2019-231917 dated Dec. 23, 2019.

* cited by examiner

MICRONEEDLE DEVICE AND METHOD FOR PRODUCING SAME

This is a National Phase Application filed under 35 U.S.C. 371 as a national stage of PCT/JP2020/047533, filed Dec. 18, 2020, an application claiming the benefit of Japanese Application No. 2019-231917, filed Dec. 23, 2019, the content of each of which is hereby incorporated by reference in its entirety.

TECHNICAL FIELD

The present invention relates to a microneedle device and a method for producing the same.

BACKGROUND ART

Dexmedetomidine is a biologically active substance that acts on the $\alpha_2$ adrenergic receptor and exhibits a sedative effect. Conventionally, a microneedle device comprising dexmedetomidine as an active component is known (for example, Patent Literature 1). A microneedle device is a device that enables percutaneous administration of a drug by puncturing the stratum corneum of the skin with microneedles to form fine pores through which the drug passes. The microneedle device generally comprises: a substrate; microneedles disposed on the substrate; and a coating formed on the microneedles, and the coating comprises a drug.

The microneedle device of Patent Literature 1 is characterized in that it comprises isoproterenol together with dexmedetomidine in the coating, thereby increasing the concentration of dexmedetomidine in the plasma after administration more rapidly.

CITATION LIST

Patent Literature

[Patent Literature 1] PCT International Publication No. WO2018/123982

SUMMARY OF INVENTION

Technical Problem

The microneedle device of Patent Literature 1 has had a problem that isoproterenol is decomposed during production or during storage after production in some cases. Therefore, the present invention aims to provide a method for producing a microneedle device comprising a coating comprising dexmedetomidine and isoproterenol, in which the stability of isoproterenol during production and after production of the microneedle device is high. In addition, the present invention also aims to provide a microneedle device produced by such a method.

Solution to Problem

A method for producing a microneedle device according to one embodiment of the present invention comprises coating microneedles with a coating liquid to form a coating on the microneedles. The microneedle device comprises a substrate, microneedles disposed on the substrate, and a coating formed on the microneedles. The coating liquid comprises dexmedetomidine or a pharmaceutically acceptable salt thereof, isoproterenol or a pharmaceutically acceptable salt thereof, ethylenediaminetetraacetic acid or a pharmaceutically acceptable salt thereof, and a sulfated polysaccharide. The sulfated polysaccharide may be chondroitin sulfate or a pharmaceutically acceptable salt thereof. The mass ratio of ethylenediaminetetraacetic acid or a pharmaceutically acceptable salt thereof to isoproterenol or a pharmaceutically acceptable salt thereof in the coating liquid may be 0.013 or more. The concentration of the sulfated polysaccharide in the coating liquid may be 0.5 mass % or more.

A microneedle device according to one embodiment of the present invention comprises a substrate, microneedles disposed on the substrate, and a coating formed on the microneedles. The coating comprises dexmedetomidine or a pharmaceutically acceptable salt thereof, isoproterenol or a pharmaceutically acceptable salt thereof, ethylenediaminetetraacetic acid or a pharmaceutically acceptable salt thereof, and a sulfated polysaccharide. The sulfated polysaccharide may be chondroitin sulfate or a pharmaceutically acceptable salt thereof. The mass ratio of ethylenediaminetetraacetic acid or a pharmaceutically acceptable salt thereof to isoproterenol or a pharmaceutically acceptable salt thereof may be 0.013 or more. The amount of the sulfated polysaccharide with respect to 100 parts by mass of the coating may be 0.5 parts by mass or more.

Advantageous Effects of Invention

According to the method of the present invention, the stability of isoproterenol during production and after production of the microneedle device becomes high by using a coating liquid comprising ethylenediaminetetraacetic acid.

In addition, according to the method of the present invention, it is possible to produce a microneedle device that carries a larger amount of dexmedetomidine and isoproterenol per microneedle, by using a coating liquid comprising a sulfated polysaccharide. This enables administration of a larger amount of dexmedetomidine per microneedle.

DESCRIPTION OF EMBODIMENTS

A method for producing a microneedle device according to one embodiment of the present invention comprises coating microneedles with a coating liquid to form a coating on the microneedles (coating step). After the coating step, drying of the coating (drying step) may be performed. Here, the microneedle device is a device comprising a substrate, microneedles disposed on the substrate, and a coating formed on the microneedles. The composition of the coating will be described later.

Figure 1:
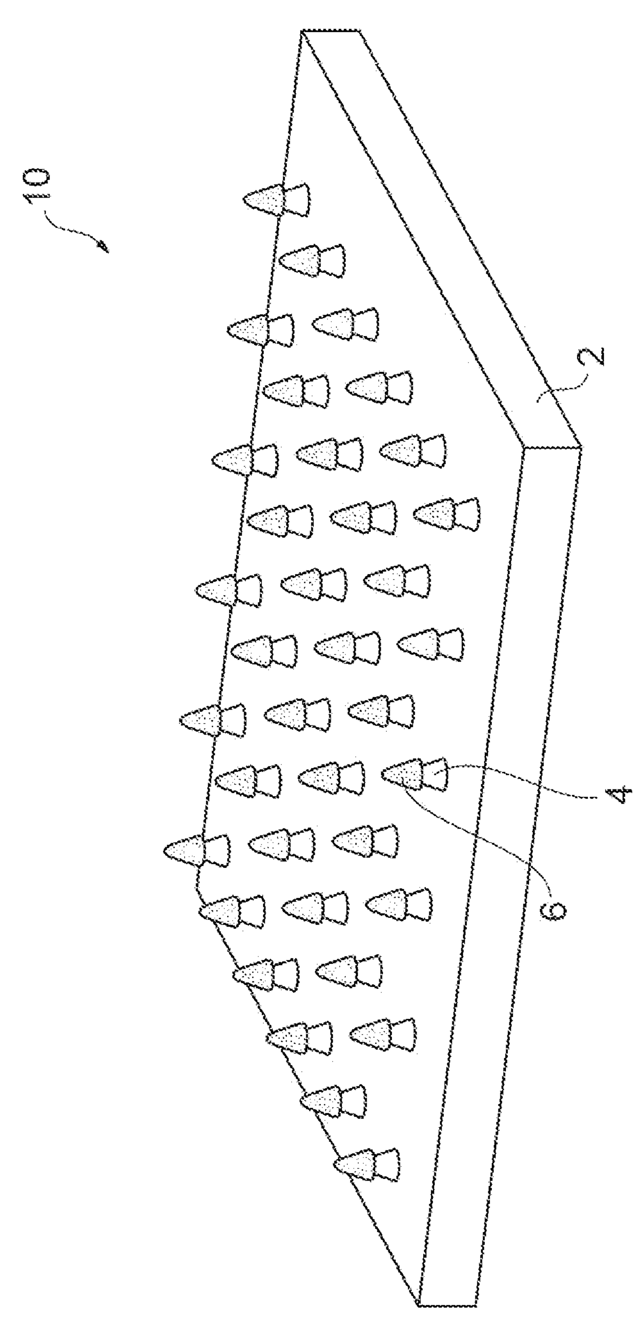
FIG. 1 is a perspective view schematically showing one embodiment of the microneedle device.

FIG. 1 shows one embodiment of the microneedle device of the present invention. A microneedle device 10 comprises a substrate 2, a plurality of microneedles 4 disposed on the main surface of the substrate 2, and a coating 6 formed on the microneedles 4. In this specification, a configuration in which a plurality of microneedles 4 are disposed on the substrate 2 is referred to as a microneedle array.

The substrate 2 is a base for supporting the microneedles 4. The shape and the form of the substrate 2 are not particularly limited, and may be, for example, a rectangle or a circle, and the main surface may be flat or curved. The area of the substrate 2 may be, for example, 0.5 $cm^2$ to 10 $cm^2$, 0.5 $cm^2$ to 5 $cm^2$, 1 $cm^2$ to 5 $cm^2$, 0.5 $cm^2$ to 3 $cm^2$, or 1 $cm^2$ to 3 $cm^2$. The thickness of the substrate 2 may be, for example, 50 μm to 2,000 μm, 300 μm to 1,200 μm, or 500 μm to 1,000 μm.

The microneedles 4 may be needle-shaped convex structures. The shape of each microneedle 4 may be, for example, a polygonal pyramid such as a quadrangular pyramid or a cone. Microneedles 4 are microstructures, and the length (height) $H_M$ of each microneedle 4 in a direction perpendicular to the main surface of the substrate 2 may be, for example, 50 μm to 600 μm, 100 μm to 500 μm, or 300 μm to 500 μm.

The microneedles 4 are disposed on the main surface of the substrate in, for example, a square lattice pattern, a rectangular lattice pattern, an orthorhombic lattice pattern, a 450 staggered pattern, or a 600 staggered pattern.

The density (needle density) at which the microneedles 4 are disposed on the substrate 2 is represented by the number of the microneedles 4 per unit area in the region substantially having the microneedles 4. The region substantially having the microneedles 4 is a region obtained by connecting the outermost microneedles 4 among the plurality of microneedles 4 disposed in the microneedle device 10. From the viewpoint of introducing a larger amount of dexmedetomidine into the skin, the needle density may be, for example, 10 needles/$cm^2$ or more, 50 needles/$cm^2$ or more, or 100 needles/$cm^2$ or more. From the viewpoint of reducing skin irritation, the needle density may be, for example, 2,000 needles/$cm^2$ or less, 850 needles/$cm^2$ or less, 500 needles/$cm^2$ or less, 200 needles/$cm^2$ or less, or 160 needles/$cm^2$ or less.

The material of the substrate 2 and the microneedle 4 may be, for example, silicon, silicon dioxide, a ceramic, a metal, a polysaccharide, or a synthetic or natural resin material. Examples of polysaccharides include pullulan, chitin, and chitosan. The resin material may be, for example, a biodegradable polymer such as polylactic acid, polyglycolide, polylactic acid-co-polyglycolide, polycaprolactone, polyurethane, or polyamino acid (for example, poly-γ-aminobutyric acid), or may be a non-degradable polymer such as polycarbonate, polymethacrylic acid, ethylene vinyl acetate, polytetrafluoroethylene, polyoxymethylene, or a cyclic olefin copolymer.

In the coating step of the method for producing the microneedle device 10 according to one embodiment of the present invention, the microneedles 4 are coated with a coating liquid to form the coating 6 on the microneedles 4. The coating liquid comprises dexmedetomidine or a pharmaceutically acceptable salt thereof, isoproterenol or a pharmaceutically acceptable salt thereof, ethylenediaminetetraacetic acid (EDTA) or a pharmaceutically acceptable salt thereof, and a sulfated polysaccharide. In this specification, unless otherwise specified, "dexmedetomidine" means "dexmedetomidine or a pharmaceutically acceptable salt thereof," "isoproterenol" means "isoproterenol or a pharmaceutically acceptable salt thereof," and "ethylenediaminetetraacetic acid" means "ethylenediaminetetraacetic acid or a pharmaceutically acceptable salt thereof."

In the present invention, dexmedetomidine is an active component, isoproterenol is a component that increases the concentration of dexmedetomidine in the plasma more rapidly, EDTA is a component that increases the stability of isoproterenol, and the sulfated polysaccharide is a component that helps to carry dexmedetomidine and isoproterenol on the microneedles 4.

The sulfated polysaccharide is a polysaccharide with a sulfuric acid bonded to a hydroxy group or an amino group. The sulfated polysaccharide may be, for example, one or more sulfated polysaccharides selected from the group consisting of chondroitin sulfate, carrageenan, fucoidan, ascophyllan, heparin, heparan sulfate, heparinoid, keratan sulfate, funoran, porphyran, agaropectin, furcellaran, rhamnan sulfate, glucuroxylorhamnan sulfate, xyloarabinogalactan sulfate, glucuronoxyloramnogalactan sulfate, arabinan sulfate, arbinorhamnan sulfate, sulfated dextran, sulfated pentosan, sulfated curdlan, sulfated cellulose, and salts thereof. The sulfated polysaccharide is preferably chondroitin sulfate or a pharmaceutically acceptable salt thereof, and more preferably sodium chondroitin sulfate.

The coating liquid comprises one or more solvents that dissolve components (that is, dexmedetomidine, isoproterenol, EDTA, and the sulfated polysaccharide) in the coating liquid. Examples of the solvents include water, polyhydric alcohol, lower alcohols, and triacetin, and water is preferable.

The coating liquid may further comprise other components (for example, a pH adjusting agent, a component that promotes entry of dexmedetomidine into the plasma, oils and fats, or an inorganic substance) besides dexmedetomidine, isoproterenol, EDTA, the sulfated polysaccharide, and the solvent, as long as the stability of isoproterenol is not impaired. However, the coating liquid preferably does not comprise a surfactant, a monosaccharide, and a disaccharide. A surfactant, a monosaccharide, and a disaccharide may reduce the surface tension and viscosity of the coating liquid, and may reduce the amount of the biologically active substance carried per microneedle 4. In addition, from the viewpoint of maintaining the stability of isoproterenol, the coating liquid preferably does not comprise ascorbic acid or a salt thereof, alpha thioglycerol, L-cysteine, or sodium metabisulfite or a salt thereof.

The concentration of dexmedetomidine in the coating liquid may be, for example, 0.5 mass % or more, 20 mass % or more, 30 mass % or more, or 40 mass % or more, and may be 60 mass % or less or 50 mass % or less. From the viewpoint of obtaining a sufficient therapeutic effect of dexmedetomidine, the concentration of dexmedetomidine in the coating liquid is preferably 0.5 mass % to 60 mass % or 5 mass % to 50 mass %, more preferably 30 mass % to 50 mass %, and still more preferably 40 mass % to 50 mass %.

The concentration of isoproterenol in the coating liquid may be, for example, 0.01 mass % or more, 0.05 mass % or more, 0.1 mass % or more, 0.2 mass % or more, 0.3 mass % or more, 1.0 mass % or more, or 1.5 mass % or more, and may be 10 mass % or less, 5 mass % or less, 2.5 mass % or less, or 1.5 mass % or less. From the viewpoint of increasing the concentration of dexmedetomidine in the plasma more rapidly, the concentration of isoproterenol in the coating liquid is preferably 0.01 mass % to 10 mass % or 0.1 mass % to 5 mass %, more preferably 0.2 to 2.5 mass %, and still more preferably 0.3 mass % to 1.5 mass %.

The concentration of EDTA in the coating liquid may be, for example, 0.01 mass % or more, 0.02 mass % or more, 0.05 mass % or more, 0.1 mass % or more, 0.5 mass % or more, 1.0 mass % or more, or 1.5 mass % or more, and may be 10 mass % or less, 5 mass % or less, 2.5 mass % or less, or 1.5 mass % or less. From the viewpoint of increasing the stability of isoproterenol, the concentration of EDTA in the coating liquid is preferably 0.01 mass % to 10 mass %, 0.02 mass % to 5 mass %, or 0.05 mass % to 5 mass %, more preferably 0.1 mass % to 2.5 mass %, and still more preferably 0.1 mass % to 1.5 mass %.

The concentration of the sulfated polysaccharide in the coating liquid may be, for example, 0.5 mass % or more, 1 mass % or more, 2 mass % or more, 4 mass % or more, 6 mass % or more, 8 mass % or more, 10 mass % or more, or 12 mass % or more, and may be 16 mass % or less, 14 mass % or less, 12 mass % or less, 10 mass % or less, 8 mass % or less, 6 mass % or less, or 4 mass % or less. From the viewpoint of allowing a larger amount of dexmedetomidine and isoproterenol to be carried per microneedle 4, the concentration of the sulfated polysaccharide in the coating liquid is preferably 0.5 mass % to 16 mass % or 1 mass % to 16 mass %, more preferably 2 mass % to 16 mass % or 2 mass % to 14 mass %, and still more preferably 4 mass % to 12 mass %.

The total concentration of the other components besides dexmedetomidine, isoproterenol, EDTA, the sulfated polysaccharide, and the solvent in the coating liquid may be, for example, 80 mass % or less, 60 mass % or less, 30 mass % or less, or 20 mass % or less. The coating liquid may comprise no other components besides dexmedetomidine, isoproterenol, EDTA, the sulfated polysaccharide, and the solvent.

The mass ratio of EDTA to isoproterenol in the coating liquid may be, for example, 0.0067 or more, 0.013 or more, 0.033 or more, 0.067 or more, 0.33 or more, 0.67 or more, or 1 or more, and may be 5 or less, 3.3 or less, or 2 or less. From the viewpoint of increasing the stability of isoproterenol, the mass ratio of EDTA to isoproterenol in the coating liquid is preferably 0.013 or more or 0.033 or more, more preferably 0.067 or more or 1 or more, and still more preferably 0.033 to 5, 0.033 to 1, or 0.067 to 1.

The mass ratio of the sulfated polysaccharide to dexmedetomidine in the coating liquid may be, for example, 0.01 or more, 0.02 or more, 0.04 or more, 0.09 or more, 0.13 or more, 0.18 or more, 0.22 or more, or 0.27 or more, and may be 0.36 or less, 0.31 or less, 0.27 or less, 0.22 or less, 0.18 or less, 0.13 or less, or 0.09 or less. From the viewpoint of allowing a larger amount of dexmedetomidine to be carried per microneedle 4, the mass ratio of the sulfated polysaccharide to dexmedetomidine in the coating liquid is preferably 0.01 to 0.36 or 0.02 to 0.36, more preferably 0.04 to 0.36 or 0.04 to 0.31, and still more preferably 0.09 to 0.27.

The mass ratio of the sulfated polysaccharide to isoproterenol in the coating liquid may be, for example, 0.3 or more, 0.7 or more, 1 or more, 3 or more, 4 or more, 5 or more, 7 or more, or 8 or more, and may be 40 or less, 27 or less, 16 or less, 11 or less, 9 or less, 8 or less, 7 or less, 5 or less, 4 or less, or 3 or less. From the viewpoint of allowing a larger amount of isoproterenol to be carried per microneedle 4, the mass ratio of the sulfated polysaccharide to isoproterenol in the coating liquid is preferably 0.3 to 11 or 0.7 to 11, more preferably 1 to 11 or 1 to 9, and still more preferably 3 to 8.

From the viewpoint of improving the rate of increase in the concentration of dexmedetomidine in the plasma, the mass ratio of isoproterenol to dexmedetomidine in the coating liquid may be 0.003 or more, 0.008 or more, 0.01 or more, 0.03 or more, or 0.07 or more. The mass ratio of isoproterenol to dexmedetomidine in the coating liquid may be 0.18 or less, 0.09 or less, 0.08 or less, 0.07 or less, or 0.03 or less, or may be 0.003 to 0.18 or 0.008 to 0.09. The mass ratio of isoproterenol to dexmedetomidine is preferably 0.008 to 0.03.

The concentration of each component contained in the coating liquid may be measured by, for example, a liquid chromatography method.

From the viewpoint of coating the microneedles 4 with a larger amount of the coating liquid and from the viewpoint of forming the coating 6 on the tip portions of the microneedles 4, the viscosity of the coating liquid at 25° C. is preferably 500 mPa-s to 30,000 mPa-s and more preferably 1,000 mPa-s to 10,000 mPa-s. From the same viewpoints, the surface tension of the coating liquid is preferably 10 mN/m to 100 mN/m, and more preferably 20 mN/m to 80 mN/m.

The coating liquid may be prepared by mixing the above components. That is, in one embodiment, the method of the present invention may comprise, before the coating step, mixing dexmedetomidine, isoproterenol, EDTA, and the sulfated polysaccharide to prepare the coating liquid. The order in which the components are mixed is not particularly limited, and for example, dexmedetomidine, isoproterenol, EDTA, the sulfated polysaccharide, and the solvent may be mixed at the same time. Alternatively, first, dexmedetomidine, EDTA and the sulfated polysaccharide may be mixed with the solvent, and then isoproterenol may be added and mixed with the mixed solution. The coating liquid may be mixed or stirred, for example, with a spatula until it is coated on the microneedles 4. The spatula is not particularly limited, and for example, a screen printing spatula such as a squeegee or a scraper may be used.

A method of coating the microneedles 4 with the coating liquid is not particularly limited, and for example, the coating liquid may be coated by inkjet coating or dip coating. Among these, dip coating is preferable. In the dip coating, the microneedles 4 are coated with the coating liquid by dipping the microneedles 4 to a certain depth in a reservoir in which the coating liquid is stored, and then withdrawing the microneedles 4 from the reservoir. According to the method of the present embodiment using the coating liquid comprising EDTA, decomposition of isoproterenol in the coating liquid in the reservoir is suppressed, even when it takes time from preparation of the coating liquid to coating of the microneedles. Namely, it is possible to stabilize isoproterenol during production of the microneedle device.

The amount of the coating liquid coated on the microneedles 4 may be adjusted by the depth to which the microneedles 4 are dipped, for example, in the case of coating by dip coating. Here, the depth to which the microneedles 4 are dipped indicates the distance from the vertex of the dipped microneedles 4 to the surface of the coating liquid. The dipping depth depends on the length $H_M$ of the microneedle 4, and may be, for example, $H_M$ or less or $H_M/2$ or less. However, among the components contained in the coating 6, the component contained in the portion formed on the base portion of the microneedle 4 is less likely to be introduced into the skin compared to the component contained in the portion formed on the tip portion of the microneedle 4. Therefore, it is preferable that a larger amount of the coating liquid is coated mainly on the tip portion of the microneedle 4. Here, as will be described below, the tip portion of the microneedle 4 is a portion in which the length measured from the vertex of the microneedle 4 in a direction perpendicular to the main surface (that is, the base portion) of the substrate 2 is, for example, within 50% of the length $H_M$ of the microneedle 4.

In the arbitrary drying step after the coating step, the coating 6 is dried. Here, drying the coating 6 means volatilizing some or all of the solvent contained in the coating 6.

The coating 6 may be dried, for example, by sealing the microneedle device 10 in a hygroscopic aluminum laminate packaging material or by a method such as air drying, vacuum drying, freeze drying, or a combination thereof. A preferable drying method is air drying.

Here, since the coating liquid according to the present invention comprising the sulfated polysaccharide has a high viscosity and surface tension, downward flowing and spreading of the coating 6 due to gravity before or during drying of the coating 6 can be further reduced. Therefore, even when the coating 6 is dried with microneedle array placed in a such a way that the microneedles 4 face upward, the coating 6 can be maintained mainly on the tip portions of the microneedles 4.

The coating step and the drying step may be repeatedly performed. The amount of the coating 6 formed can be further increased by repeating these steps.

The microneedle device 10 according to one embodiment of the present invention produced by the above method comprises the coating 6 comprising dexmedetomidine, isoproterenol, EDTA, and the sulfated polysaccharide on the microneedles 4.

Details of the microneedle array, dexmedetomidine, isoproterenol, EDTA, and the sulfated polysaccharide constituting the microneedle device 10 are as described above. The above described coating liquid and the coating 6 comprise the same components except for the solvent. However, the coating 6 may comprise the above described solvent.

The amount of dexmedetomidine with respect to 100 parts by mass of the coating 6 may be, for example, 10 parts by mass or more, 40 parts by mass or more, 45 parts by mass or more, or 60 parts by mass or more, and may be 90 parts by mass or less or 85 parts by mass or less. From the viewpoint of obtaining a sufficient therapeutic effect of dexmedetomidine, the amount of dexmedetomidine with respect to 100 parts by mass of the coating 6 is preferably 10 parts by mass to 90 parts by mass or 40 parts by mass to 85 parts by mass, more preferably 45 parts by mass to 85 parts by mass, and still more preferably 60 parts by mass to 85 parts by mass.

The amount of isoproterenol with respect to 100 parts by mass of the coating 6 may be, for example, 0.2 parts by mass or more, 0.6 parts by mass or more, 0.8 parts by mass or more, 1.5 parts by mass or more, 2.4 parts by mass or more, or 4.8 parts by mass or more, and may be 12 parts by mass or less, 9 parts by mass or less, 5.5 parts by mass or less, 5.0 parts by mass or less, 4.8 parts by mass or less, or 2.7 parts by mass or less. From the viewpoint of increasing the concentration of dexmedetomidine in the plasma more rapidly, the amount of isoproterenol with respect to 100 parts by mass of the coating 6 is preferably 0.2 parts by mass to 12 parts by mass or 0.6 parts by mass to 9 parts by mass, more preferably 0.6 parts by mass to 5 parts by mass, and still more preferably 0.6 to 2.7 parts by mass.

The amount of EDTA with respect to 100 parts by mass of the coating 6 may be, for example, 0.02 parts by mass or more, 0.04 parts by mass or more, 0.09 parts by mass or more, 0.2 parts by mass or more, 0.9 parts by mass or more, 1.8 parts by mass or more, or 2.7 parts by mass or more, and may be 10 parts by mass or less, 6 parts by mass or less, 4 parts by mass or less, or 2.7 parts by mass or less. From the viewpoint of increasing the stability of isoproterenol, the amount of EDTA with respect to 100 parts by mass of the coating 6 is preferably 0.01 parts by mass to 10 parts by mass, 0.02 parts by mass to 6 parts by mass, or 0.04 parts by mass to 6 parts by mass, more preferably 0.2 parts by mass to 4 parts by mass, and still more preferably 0.2 parts by mass to 2.7 parts by mass.

The amount of the sulfated polysaccharide with respect to 100 parts by mass of the coating 6 may be, for example, 1 part by mass or more, 2 parts by mass or more, 4 parts by mass or more, 8 parts by mass or more, 11 parts by mass or more, 15 parts by mass or more, 18 parts by mass or more, or 20 parts by mass or more, and may be 25 parts by mass or less, 23 parts by mass or less, 20 parts by mass or less, 18 parts by mass or less, 15 parts by mass or less, 11 parts by mass or less, or 8 parts by mass or less. From the viewpoint of allowing a larger amount of dexmedetomidine and isoproterenol to be carried per microneedle 4, the amount of the sulfated polysaccharide with respect to 100 parts by mass of the coating 6 may be, for example, 1 part by mass to 25 parts by mass, 2 parts by mass to 25 parts by mass, 4 parts by mass to 25 parts by mass, 4 parts by mass to 23 parts by mass, or 8 parts by mass to 20 parts by mass.

The total amount of the other components besides dexmedetomidine, isoproterenol, EDTA, the sulfated polysaccharide, and the solvent with respect to 100 parts by mass of the coating 6 may be, for example, 95 parts by mass or less, 75 parts by mass or less, 50 parts by mass or less, or 30 parts by mass or less. The coating 6 may comprise no other components besides dexmedetomidine, isoproterenol, EDTA, the sulfated polysaccharide, and the solvent.

The mass ratio of EDTA to isoproterenol, the mass ratio of the sulfated polysaccharide to dexmedetomidine, the mass ratio of the sulfated polysaccharide to isoproterenol, and the mass ratio of isoproterenol to dexmedetomidine are as described above. Namely, these mass ratios may be the same as the mass ratios in the coating liquid.

The amount of the coating 6 carried per microneedle 4 may be, for example, 10 ng to 10,000 ng, 490 ng to 700 ng, 516 ng to 642 ng, 456 ng to 836 ng, or 819 ng to 836 ng. From the viewpoint of exhibiting a sufficient medicinal effect, the amount of dexmedetomidine carried per microneedle 4 may be 390 ng or more, 451 ng or more, or 670 ng or more. The upper limit of the amount of dexmedetomidine carried per microneedle 4 is not particularly limited, and may be, for example, 2 μg or less, 1 μg or less, 755 ng or less, 545 ng or less or 500 ng or less. The amount of isoproterenol carried per microneedle 4 may be, for example, 0.1 ng to 100 ng, 0.6 ng to 25 ng, or 0.4 ng to 25 ng.

The amount of each component contained in the coating 6 may be measured by, for example, a liquid chromatography method.

When there are a plurality of microneedles 4, the coating 6 may be formed on all the microneedles 4, or may be formed only on some of the microneedles 4. The coating 6 may be formed only on a portion of the microneedle 4 or may be formed to cover the entire microneedle 4. The coating 6 is preferably formed on the tip portion of the microneedle 4. Here, the tip portion of the microneedle 4 is a portion in which the length measured from the vertex of the microneedle 4 in a direction perpendicular to the main surface (that is, the base portion) of the substrate 2 is within 50%, within 40%, within 30%, or within 20% of the length $H_M$ of the microneedle 4. The average thickness of the coating 6 may be less than 100 μm, less than 50 μm, or 1 μm to 30 μm.

EXAMPLES

<Test Example 1-1> Stability of Isoproterenol in Microneedle Device

Microneedle devices were produced using different stabilizers, and the stability of isoproterenol hydrochloride after 1 month was evaluated as follows.

A coating liquid having a composition shown in Table 1 was prepared, the coating liquid was filled into a reservoir, and mixing was performed with a squeegee for 60 minutes. A polylactic acid microneedle array in which microneedles were provided in a region of 1 cm$^2$ with a density of 156 needles/cm$^2$, and the shape of each microneedle was a quadrangular pyramid with a height of 500 μm was prepared, and the tips of the microneedles were dipped in the coating liquid in the reservoir.

After the microneedles were withdrawn from the coating liquid, the microneedle device was sealed in a hygroscopic aluminum laminate packaging material, and stored under conditions of 50° C. and 75% RH. After storage for 1 month, the coating on the microneedles was extracted, and isoproterenol hydrochloride and an isoproterenol analog in the extract were quantified by high performance liquid chromatography (HPLC).

The HPLC conditions are as follows:

Column: ODS 80 Ts QA5 μm (4.6 mm I. D.×150 mm)
Flow rate: 0.5 mL/min
Measurement wavelength: 280 nm The amount of isoproterenol hydrochloride in the coating (%) represented by Formula 1 below and the production rate (%) of the isoproterenol analog represented by Formula 2 below were calculated, and based on these results, the stability of isoproterenol hydrochloride in the coating was evaluated. The results are shown in Table 1. Here, the "peak area" in Formula 2 is a peak area in the result of HPLC after storage for 1 month. The relative retention time (RRT) of the isoproterenol analog with respect to isoproterenol hydrochloride was about 1.05.

Amount of isoproterenol hydrochloride in the coating (%)=Amount of isoproterenol hydrochloride in the coating after storage for 1 month/Amount of isoproterenol hydrochloride in the coating before storage for 1 month×100 (Formula 1):

Production rate of the isoproterenol analog (%)=Peak area of the isoproterenol analog/Peak area of isoproterenol hydrochloride×100 (Formula 2):

TABLE 1

| | Comparative Example 1 | Example 1 | Comparative Example 2 | Comparative Example 3 | Comparative Example 4 | Comparative Example 5 |
|---|---|---|---|---|---|---|
| Dexmedetomidine hydrochloride | 45 | 45 | 45 | 45 | 45 | 45 |
| IP hydrochloride | 1.5 | 1.5 | 1.5 | 1.5 | 1.5 | 1.5 |
| Chondroitin sulfate Na | 8 | 8 | 8 | 8 | 8 | 8 |
| Water for injection | 45.5 | 45 | 45 | 45 | 45 | 45 |
| EDTA•2Na | — | 0.5 | — | — | — | — |
| L-cysteine | — | — | 0.5 | — | — | — |
| Ascorbic acid | — | — | — | 0.5 | — | — |
| Sodium metabisulfite | — | — | — | — | 0.5 | |
| Alpha thioglycerol | — | — | — | — | — | 0.5 |
| Total amount (mass %) | 100 | 100 | 100 | 100 | 100 | 100 |
| Amount (%) of IP hydrochloride in coating | 92.8 | 95.4 | 94.7 | 94.2 | 95.2 | 91.5 |
| Production rate (%) of IP analog | 3.5 | 2.1 | 2.2 | 1.3 | 4.1 | 10.5 |
| Stability of IP hydrochloride (after production) | B | A | A | A | B | B |

In the tables in this specification, "IP" indicates isoproterenol, "chondroitin sulfate Na" indicates sodium chondroitin sulfate, and "EDTA·2Na" indicates ethylenediaminetetraacetic acid disodium. In Table 1, the microneedle devices with high isoproterenol hydrochloride stability were evaluated as A, and the microneedle devices with insufficient isoproterenol hydrochloride stability were evaluated as B. As shown in Table 1, in the microneedle devices comprising ethylenediaminetetraacetic acid disodium, L-cysteine or ascorbic acid in the coating, the stability of isoproterenol hydrochloride after production was high.

<Test Example 1-2> Stability of Isoproterenol During Production

Microneedle devices were produced using different stabilizers, and the stability of isoproterenol hydrochloride during production (1 to about 24 hours) was evaluated as follows. This test was conducted under conditions of a temperature of 19 to 23° C. and a humidity of 79 to 83% RH. The microneedle array used in this test was the same as the microneedle array used in Test Example 1-1.

A coating liquid having a composition shown in Table 2 was prepared, the coating liquid was filled into a reservoir, and mixing was performed with a squeegee for 60 minutes.

After 60 minutes, the tips of the microneedles in the microneedle array were dipped in the coating liquid in the reservoir and then withdrawn to coat the microneedles with the coating liquid. Isoproterenol hydrochloride and an isoproterenol analog in the coating of the obtained microneedle device were quantified.

After an additional 75 minutes (that is, 135 minutes after the coating liquid was prepared), the tips of the microneedles of a new microneedle array were dipped in the coating liquid in the reservoir and then withdrawn, and isoproterenol hydrochloride and the isoproterenol analog in the coating of the obtained microneedle device were quantified. Microneedles were produced and evaluated every 75 minutes in the same manner.

Figure 2:
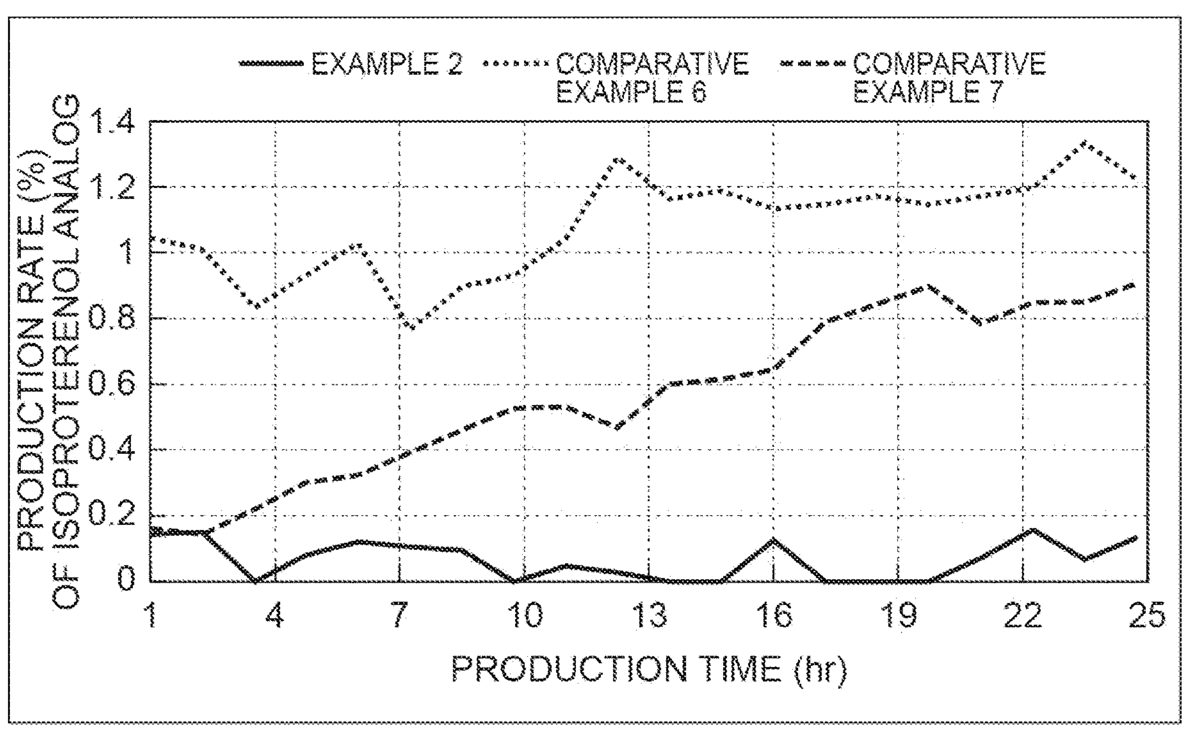
FIG. 2 is a graph showing the relationship between the time required for producing a microneedle device and the production rate of an isoproterenol analog.

For each of the produced microneedle devices, the production rate (%) of the isoproterenol analog represented by Formula 3 below was calculated. FIG. 2 is a graph showing the production rate of the isoproterenol analog with respect to the time from preparation of the coating liquid to coating of the microneedle (that is, the production time). In addition, the stability of isoproterenol hydrochloride during production was evaluated, based on the production rate (%) of the isoproterenol analog and the appearance of the coating of the microneedle device in which the coating liquid was coated on about 24 hours after the coating liquid was prepared (Namely, having the production time of about 24 hours). The results are shown in Table 2. Here, the "peak area" in Formula 3 is a peak area in the result of HPLC for each microneedle device. The relative retention time (RRT) of the isoproterenol analog with respect to isoproterenol hydrochloride was about 1.05.

$$\text{Production rate of the isoproterenol analog } (\%) = \text{Peak area of the isoproterenol analog}/\text{Peak area of isoproterenol hydrochloride} \times 100 \quad \text{(Formula 3)}:$$

TABLE 2

| | Example 2 | Comparative Example 6 | Comparative Example 7 |
|---|---|---|---|
| Dexmedetomidine hydrochloride | 45 | 45 | 45 |
| IP hydrochloride | 1.5 | 1.5 | 1.5 |
| Chondroitin sulfate Na | 8 | 8 | 8 |
| Water for injection | 44.5 | 40.5 | 44.5 |
| EDTA•2Na | 1 | — | — |
| L-cysteine | — | 5 | — |
| Ascorbic acid | — | — | 1 |
| Total amount (mass %) | 100 | 100 | 100 |
| Production rate (%) of IP analog | 0.13 | 1.2 | 0.9 |
| Appearance of coating | Transparent | Transparent | Brown |
| Stability of IP hydrochloride (during production) | A | B | B |

In Table 2, a case where the stability of isoproterenol hydrochloride during production was high was evaluated as A, and cases where the stability of isoproterenol hydrochloride during production was not sufficient were evaluated as B. As shown in Table 2, in Example 2 in which ethylenediaminetetraacetic acid disodium was added to the coating liquid, decomposition of isoproterenol hydrochloride was suppressed, even when it took about 24 hours from preparation of the coating liquid to coating of the microneedles. On the other hand, in Comparative Example 6 in which L-cysteine was added to the coating liquid, the production rate of the isoproterenol analog was high, suggesting a decomposition of isoproterenol hydrochloride. In Comparative Example 7 in which ascorbic acid was added to the coating liquid, not only was the production rate of the isoproterenol analog high, but the coating also turned brown, suggesting a decomposition of isoproterenol hydrochloride into a plurality of analogs.

<Test Example 1-3> Stability of Isoproterenol in Microneedle Device

Microneedle devices were produced using ethylenediaminetetraacetic acid disodium and isoproterenol hydrochloride of different concentrations, and the stability of isoproterenol hydrochloride after 1 to 2 months was evaluated as follows.

Microneedle devices were produced and the production rate (%) of the isoproterenol analog after storage for 1 month was calculated in the same manner as in Test Example 1-1, except that the composition of the coating liquid was changed to the composition shown in Table 3 and Table 4. In addition, the same test was conducted with the storage period of the microneedle devices extended to 2 months. The results are also shown in Table 3 and Table 4.

TABLE 3

| | Comparative Example | Examples | | | | | |
|---|---|---|---|---|---|---|---|
| | 1 | 3 | 4 | 5 | 1 | 6 | 7 |
| Dexmedetomidine hydrochloride | 45 | 45 | 45 | 45 | 45 | 45 | 45 |
| IP hydrochloride | 1.5 | 1.5 | 1.5 | 1.5 | 1.5 | 1.5 | 1.5 |
| Chondroitin sulfate Na | 8 | 8 | 8 | 8 | 8 | 8 | 8 |
| EDTA•2Na | — | 0.01 | 0.05 | 0.1 | 0.5 | 1 | 1.5 |
| Water for injection | 45.5 | 45.49 | 45.45 | 45.4 | 45 | 44.5 | 44 |
| Total amount (mass %) | 100 | 100 | 100 | 100 | 100 | 100 | 100 |
| EDTA•2Na/ IP hydrochloride | — | 0.0067 | 0.033 | 0.067 | 0.33 | 0.67 | 1 |
| Production rate (%) of IP analog (after storage for 1 month) | 3.5 | 2.8 | 2.1 | 2 | 2.1 | 2.1 | 1.5 |

TABLE 3-continued

| | Comparative Example | Examples | | | | | |
|---|---|---|---|---|---|---|---|
| | 1 | 3 | 4 | 5 | 1 | 6 | 7 |
| Production rate (%) of IP analog (after storage for 2 months) | 6.7 | 5.4 | 4 | 3.8 | 3.8 | 4.1 | 3.3 |

TABLE 4

| | Examples | | | |
|---|---|---|---|---|
| | 18 | 19 | 20 | 21 |
| Dexmedetomidine hydrochloride | 45 | 45 | 45 | 45 |
| IP hydrochloride | 1.5 | 0.5 | 0.3 | 0.2 |
| Chondroitin sulfate Na | 8 | 8 | 8 | 8 |
| EDTA•2Na | 0.02 | 1 | 1 | 1 |
| Water for injection | 45.48 | 45.5 | 45.7 | 45.8 |
| Total amount (mass %) | 100 | 100 | 100 | 100 |
| EDTA•2Na/IP hydrochloride | 0.013 | 2 | 3.3 | 5 |
| Production rate (%) of IP analog (after storage for 1 month) | 2.6 | 1.7 | 1.5 | 1.7 |
| Production rate (%) of IP analog (after storage for 2 months) | 4.2 | 3.6 | 3.1 | 3.1 |

Test Example 1—Results

From the results of Test Examples 1-1 to 1-3, it was shown that, when a microneedle device is produced using a coating liquid comprising ethylenediaminetetraacetic acid disodium, the stability of isoproterenol hydrochloride during production and after production becomes high. On the other hand, it was also shown that, when a microneedle device is produced using a coating liquid comprising a stabilizer other than EDTA, the stability of isoproterenol hydrochloride during production or after production is not sufficient. In addition, from the results of Test Example 1-3, it was shown that, when a ratio of ethylenediaminetetraacetic acid disodium to isoproterenol hydrochloride is at a certain level or above, the stability of isoproterenol hydrochloride after production becomes higher.

<Test Example 2> Amount of Dexmedetomidine and Isoproterenol Carried

A coating liquid having a composition shown in Table 5 was prepared, the coating liquid was filled into a reservoir, and mixing was performed with a squeegee for 60 minutes. The same microneedle array as the microneedle array used in Test Example 1 was prepared, and the tips of the microneedles were dipped to a depth of about 140 μm in the coating liquid of the reservoir. After withdrawing the microneedles from the coating liquid, the coating on the microneedles was dried.

The amount of dexmedetomidine hydrochloride and isoproterenol hydrochloride in the coating formed on the microneedles was quantified by HPLC, and the amount of dexmedetomidine hydrochloride and isoproterenol hydrochloride per microneedle was calculated therefrom. The results are shown in Table 5.

TABLE 5

| | Examples | | | | | | | | | |
|---|---|---|---|---|---|---|---|---|---|---|
| | 8 | 9 | 10 | 11 | 12 | 13 | 14 | 15 | 16 | 17 |
| Dexmedetomidine hydrochloride | 45 | 45 | 45 | 45 | 45 | 45 | 45 | 45 | 45 | 45 |
| IP hydrochloride | 1.5 | 1.5 | 1.5 | 1.5 | 1.5 | 1.5 | 1.5 | 1.5 | 1.5 | 1.5 |
| Chondroitin sulfate Na | 0.5 | 1 | 2 | 4 | 6 | 8 | 10 | 12 | 14 | 16 |
| EDTA•2Na | 0.5 | 0.5 | 0.5 | 0.5 | 0.5 | 0.5 | 0.5 | 0.5 | 0.5 | 0.5 |
| Water for injection | 52.5 | 52 | 51 | 49 | 47 | 45 | 43 | 41 | 39 | 37 |
| Total amount (mass %) | 100 | 100 | 100 | 100 | 100 | 100 | 100 | 100 | 100 | 100 |
| Chondroitin sulfate Na/ Dexmedetomidine hydrochloride (before coating) | 0.01 | 0.02 | 0.04 | 0.09 | 0.13 | 0.18 | 0.22 | 0.27 | 0.31 | 0.36 |
| Chondroitin sulfate Na/ IP hydrochloride (before coating) | 0.3 | 0.7 | 1 | 3 | 4 | 5 | 7 | 8 | 9 | 11 |
| Amount of dexmedetomidine hydrochloride (ng/needle) | 340 | 361 | 467 | 573 | 623 | 540 | 565 | 551 | 462 | 428 |
| Amount of IP hydrochloride (ng/needle) | 11 | 11 | 15 | 19 | 21 | 18 | 19 | — | 15 | 14 |

As shown in Table 5, a larger amount of dexmedetomidine hydrochloride was able to be carried per microneedle by adding a specific amount of sodium chondroitin sulfate to the coating liquid.

REFERENCE SIGNS LIST

2 Substrate
4 Microneedle
6 Coating
10 Microneedle device

The invention claimed is:

1. A method for producing a microneedle device comprising a substrate, microneedles disposed on the substrate, and a coating formed on the microneedles, the method comprising:

coating the microneedles with a coating liquid to form the coating on the microneedles, wherein the coating liquid comprises:

dexmedetomidine or a pharmaceutically acceptable salt thereof in a concentration of 40 mass % to 60 mass %, isoproterenol or a pharmaceutically acceptable salt thereof in a concentration of 0.2 mass % to 1.5 mass %, ethylenediaminetetraacetic acid or a pharmaceutically acceptable salt thereof in a concentration of 0.02 mass % to 1.5 mass %, and a sulfated polysaccharide in a concentration of 0.5 mass % to 16 mass %;

wherein the sulfated polysaccharide is chondroitin sulfate or a pharmaceutically acceptable salt thereof; and wherein a mass ratio of the ethylenediaminetetraacetic acid or the pharmaceutically acceptable salt thereof to the isoproterenol or the pharmaceutically acceptable salt thereof in the coating liquid is 0.013 or more.

2. A microneedle device comprising a substrate, microneedles disposed on the substrate, and a coating formed on the microneedles, wherein the coating comprises:

dexmedetomidine or a pharmaceutically acceptable salt thereof in an amount with respect to 100 parts by mass of 60 to 94.74 parts by mass, isoproterenol or a pharmaceutically acceptable salt thereof in an amount with respect to 100 parts by mass of 0.2 to 4.8 parts by mass, ethylenediaminetetraacetic acid or a pharmaceutically acceptable salt thereof in an amount with respect to 100 parts by mass of 0.04 to 2.7 parts by mass, and a sulfated polysaccharide in an amount with respect to 100 parts by mass of 1 to 25 parts by mass;

wherein the sulfated polysaccharide is chondroitin sulfate or a pharmaceutically acceptable salt thereof; and wherein a mass ratio of the ethylenediaminetetraacetic acid or the pharmaceutically acceptable salt thereof to the isoproterenol or the pharmaceutically acceptable salt thereof is 0.013 or more.

* * * * *